Aug. 20, 1968 L. M. RANTZ ETAL Plant Pat. 2,828
HYBRID TEA ROSE
Filed Nov. 30, 1966
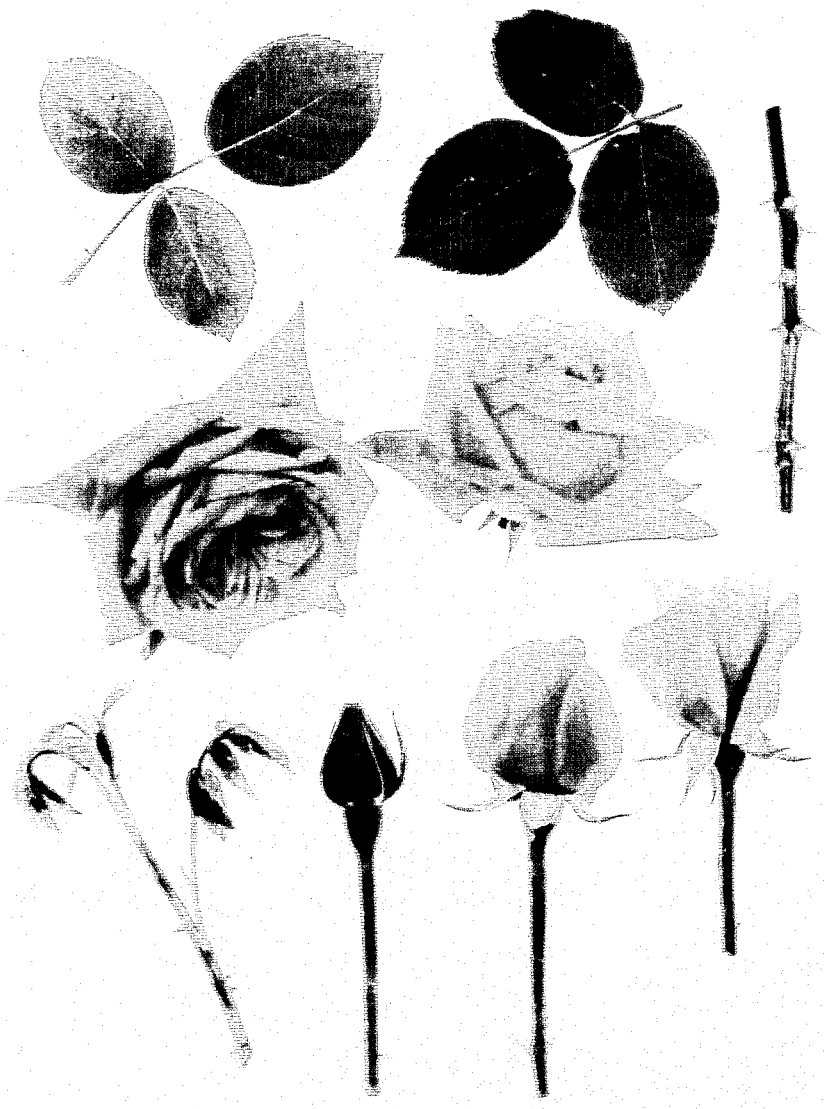

United States Patent Office

Plant Pat. 2,828
Patented Aug. 20, 1968

2,828
HYBRID TEA ROSE

Louis M. Rantz and Simone Rantz, née Gastaldi, both of Roseraie des Breguieres, Cros-de-Cagnes, France

Filed Nov. 30, 1966, Ser. No. 598,130
Claims priority, application France, Feb. 28, 1966, 7,750
1 Claim. (Cl. Plt.—20)

The present description concerns a new and distinct variety of rose plant that was originated by the petitioner during a series of studies and researches made in order to obtain a new rose plant, different from the other varieties of its class, and specially suitable for indoor and outdoor cut flower culture, but able also to give beautiful plants for the ornament of parks and gardens.

The inventor sought to obtain a new rose plant with the following salient characteristics: large and beautiful flowers, of a special tonality of red colour, much appreciated in the international markets of cut flowers, borne on long and strong stems; abundant and large foliage, resistant to the chief diseases which affect cultured roses; very vigorous vegetation, able to give a high productivity in cut flowers and to produce strong bushes for ornamental purposes; easy culture in the different types of soil, and easy grafting on the chief budding stocks employed in the industrial culture.

The plant of the present invention has, in the highest degree, all these characteristics, and being different from all the other varieties already known, it constitutes an improvement in comparison with them.

The plant of the present invention has been originated through the crossing of the variety named "Marrakesch," taken as mother plant, with the variety known under the name of "Spartan," taken as father plant. The new variety of the present invention is different from the parent plants, from which, nevertheless, it has taken its best characteristics. From the mother plant, "Marrakesch," it has taken chiefly a part of the colour of the bloom, which was also influenced by the colour of the father plant, and the large and full flower. From the father plant, "Spartan," the new plant has taken chiefly a part of the growing habit and the large, dark foliage.

The plant of the present invention may be easily reproduced and multiplied, even on an industrial scale, by grafting its buds on proper stocks, getting by this way adult plants, suitable for production of cut flowers or of ornamental flowering plants.

Multiplied by this method for several years in Cagnes-sur-Mer (A.M.), France, and grafted on different stocks (*Rosa indica major, Rosa canina, Rosa laxa*) the variety following the present invention has constantly and truly transmitted in the successive generations all its distinctive characteristics.

The following description shows the characteristics that, in their unique combination, distinguish the plant of the present invention from the other varieties of its class, and allow its identification.

The description was made during the month of January, after plants industrially cultivated in a sunny ground in Cagnes-sur-Mer (A.M.), France, grafted on *Rosa indica major,* for about two years and grown outdoors and in a greenhouse.

It is always necessary to refer to the above indicated culture conditions each time it is desired to compare the plant with the present description. Whatever differences that, because of different conditions of climate, soil or culture methods, may arise between some characteristic of the plant and the corresponding characteristic given in the description, must be considered as normal, and do not modify the essence of the present invention, at least until when, repeating the culture in the same conditions of the described plants, it is possible to identify the plant by means of the whole of the characteristics given in the description.

The nomenclature of the colours of the description has been made following the tables of the "Horticultural Colour Chart" of Robert F. Wilson (indicated in the text with the initials HCC), except when the colour is missing from these tables, or when its definition was sufficiently clear by the usual description.

Classification: Tea hybrid.
Parents: "Marrakesch"×"Spartan."

*Plant*

Growing habit: Bushy, upright, vigorous, a little spread.

Average height: 2 m. (6 ft.) to 2.50 m. (8 ft.) for plants, grafted for two years on *Rosa indica major,* fully developed, cultivated in a greenhouse. One meter (3 ft.) to 1.50 m. (5 ft.), for plants in the same conditions, but grown outdoors.

Stalk: Variable in size with the stock employed in the culture. Average length, for the described plants—25–30 cms. (¾–1 ft.). Average diameter—10–15 mm. (⅜–⅝ in.).

Main branches: Numerous, starting from the budding point, moderately divergent, erect, strong, usually 4–8, rigid, or a little flexible.

*Size.*—Varies from a plant to another. Average length—30–50 cm. (1–1¾ ft.). Average diameter, at the base—10–15 mm. (⅜–⅝ in.).

*Skin.*—Smooth, glabrous, moderately thick, a little satiny.

*Colour.*—Between Parsley Green (HCC, page 198, tones 62–62/1) and Sage Green (HCC, page 198, tones 61–61/1), sometimes covered by blending of Hazelnut Brown.

*Thorns.*—Numerous, or very numerous, crowded, greatly variable in size, spread on the branches, triangular, irregular, sharp pointed, perpendicular to the branch or bent downwards. Average length—4–12 mm. (3/16–½ in.). Average breadth—8–20 mm. (⅜–¾ in.). Average thickness—2–5 mm. (1/16–¼ in.).

*Prickles.*—Numerous, generally little, short, straight or bent downwards, mixed with the thorns. Thorn texture—rigid, resistant, woody. Thorn colour—Pod Green (HCC, page 120, tones 61–61/1–2) strongly covered by colour between Garnet Brown (HCC, page 192, tones 18–18/1–2–3) and Purple Madder (HCC, page 181, tones 28–28/1–2–3) on the sides.

Floral stems: Numerous; strong, vigorous, starting from the upper part of the main branches, generally 4–6 each branch, moderately divergent, approximately cylindrically straight or a little sinuous.

*Size.*—70–120 cm. (2–4 ft.) long. Average diameter, at the base—8–12 mm. (5/16–½ in.).

*Colour.*—Between Parsley Green (HCC, page 193, tones 62–62/1–2–3) and Spinach Green (HCC, page 187, tones 60–60/1) largely covered by Garnet Brown (HCC, page 192, tones 18–18/1–2–3).

*Skin.*—Smooth, glabrous, a little satiny.

*Texture.*—Thick, woody, rigid.

*Thorns.*—Less numerous than on the main branches, more frequent at the base of the stems, spread on the internodes, large, triangular, asymmetrical, sharp-pointed, a little bent downwards. Size—8–12 mm. (5/16–½ in.) long; 12–16 mm. (½–⅝ in.) broad; 2–4 mm. (3/16–⅜ in.) thick. Colour—Pod Green (HCC, page 120, tones 61/1–2–3) covered by Garnet Brown (HCC, page 192, tones 18–18/

1–2–3), and by Purple Madder (HCC, page 18, tones 28–28/1–2–3). Prickles—numerous, amongst the thorns, little in size, regular, woody, sharp pointed.

Foliage: Abundant, dark, moderately leathery, spread on the branches and stems, medium size or large.

Leaves: Compound, 3–5–7 opposite leaflets, plus a terminal leaflet, on a sturdy rachis. Leaves are frequently abnormal, bearing only a leaflet instead of two, in the pair at the base of the leaf, and often the opposite peduncles of a pair are not inserted at the same point on the rachis.

*Size.*—Varies with the position on the plant, decreasing a little from the base to the top. Average length—150–200 mm. (6–8 in.) from the base of the rachis to the point of the terminal leaflet. Average breadth—80–120 mm. (3–5 in.) between the extreme points of the opposite leaflets.

*Growing habit.*—Divergent from the stem, a little bent downwards, especially in the point of the terminal leaflet, which is often curled.

*Leaflets.*—Oval—lanceolated, moderately pointed, flat or convex upwards. Edges finely serrated. Size—varies with the position in the leaf, generally increasing from the base to the terminal leaflet. Average sizes: First pair, from the base, length—20–35 mm. (¾–1⅝ ins.); breadth—10–18 mm. (⅜–⅝ in.). Second pair, length—35–55 mm. (1⅜–2⅝ ins.); breadth—25–35 mm. (1–1⅜ ins.). Third pair, length—45–60 mm. (1⅝–2⅜ ins.); breadth—30–40 mm. (1 3/16–1⅜). Terminal leaflet, length—50–65 mm. (2–2⅜ ins.); breadth—35–40 mm. (1⅜–1½ ins.). Colour—upper face—between Parsley Green (HCC, page 193, tones 62–62/1) and Ivy Green (HCC, page 200, tones 60/2–3). Texture—medium thick, tender, resistant. Growing habit—generally flat in the plane of the leaf, or bent downwards in the lateral leaflets. Rachis—strong, straight, or a little tortuous, hollowed longitudinally in the upper face, with glandular hairs on the edges. Generally without thorns in the lower face. Stipules—adnate to the base of the rachis, large, hairy and serrated on the edges. Terminal points of the stipules divergent from the rachis at angles of 40–50°.

*Flower*

Growing habit: Erect; straight, single, terminal on the stem, sometimes accompanied by secondary buds borne on lateral stems inserted on the upper part of the stem.

Floral Peduncle: Very long, strong, upright, bearing rare, short and tender prickles.

Floral bud: Ovoid, with a conic point and irregular foliaceous appendices on the points of sepals, and other lateral appendices, thin and lanceolated, on the edges of the sepals.

*Average size.*—Length—18–25 mm. (¾–1 in.). Breadth—15–20 mm. (⅝–10/16 in.).

Calyx: Large, early open, bent downwards when corolla opens. Receptacle—large, conic, a little hollowed at the base of the sepals. Sepals—5 in number, triangular or a little lanceolated, concave longitudinally in the upper face, long pointed, with terminal irregular foliaceous appendices, and lateral, little appendices divergent from the edges. Edges—hairy or tomentous. Average size: length—25–35 mm. (1–1⅜ ins.); breadth, at the base—8–10 mm. (5/16–7/16 in.).

*Colour.*—Upper side—next to Sage Green (HCC, page 199, tones 61–61/1) almost entirely shaded by Garnet Brown (HCC, page 192, tones 18–18/1–2–3), and covered by a fine woody tomentum. Under face—glandular, Spinach Green (HCC, page 187, tones 60–60/1–2–3).

*Texture.*—Thin, herbaceous or coriaceous, resistant.

Half open bud: Ovoid, moderately long, conic at the beginning of opening, then urn-shaped, with outer petals bent outward. Edges of the outer petals curling, as corol opens.

*Average sizes.*—Length—35–45 mm. (1⅞–1 14/16 ins.). Diameter—25–40 mm. (1–1 9/16 ins.).

*Colour.*—Between Currant Red (HCC, page 167, tones 21–21/1–2–3) and Chrysanthemum Crimson (HCC, page 169, tones 24–24/1).

Open corol: Cup shaped, hemispheric. Edges of the outer petals rolled downwards, forming points. Outline of the corolla round, star shaped for the presence of the points in the petals' edges. Centre of the corolla flat, or a little concave. Irregular petals in the centre of the flower.

*Average size.*—Diameter, when fully open—90–110 mm. (3½–4⅞ ins.).

*Colour, for flowers cut half a day.*—Between Currant Red (HCC, page 167, tones 21/2–3) and Blood Red (HCC, page 166, tones 20–20/1–2–3) on the outer petals, and Red Rose (HCC, page 158, tones 24/2–3) in the center of the flower.

Petals: Numerous, average number—40–60, rounded, almost circular, concave in the center. Lateral edges converging into the attachment. Outer edge rolled outwards, forming 1–3 acute points. Central petals—irregular, often folded longitudinally.

*Average size.*—Outer petals, length—45–60 mm. (1 10/16–2⅝ ins.). Inner petals, length—25–35 mm. (1–1¼ ins.). Outer petals, breadth—50–60 mm. (2–2.6 ins.). Inner petals, breadth—30–50 mm. (1 7/16–2 ins.).

*Colour.*—Upside—between Currant Red (HCC, page 167, tones 21/2–3) and Turkey Red (HCC, page 94, tones 21/2–3) with tonalities of Red Rose (HCC, page 94, tones 24/2–3) near the attachment. Under side—between Turkey Red (HCC, page 94, tones 21/2–3) and Spirea Red (HCC, page 112, tones 25–25/1). Attachment—Lemon Yellow (HCC, page 4, tone 4/3).

*Surface.*—Upside—smooth, glabrous, satiny or light velvety. Fine veins hollowed in the petals. Under side—satiny, glabrous, little veins salient on the petals.

*Texture.*—Medium thick, resistant.

Reproductive organs: Stamens—numerous, about 90–110, on the edge of the receptacle. Filaments—thin or very thin, erect, 6–15 mm. (¼–⅝ in.) long, chrome yellow in colour. Anthers—medium sized, yellow with tonalities of rose. Styles—medium numerous, at the centre of the receptacle. Average number 90–100, crowded at their base, divergent on their top. Colour—yellow washed with red. Stigma—narrow, funnel shaped. Chrome yellow in colour.

Scent: Sweet; characteristic hybrid tea.

Bloom: Abundant, all the year long.

Resistance of flowers to transport: Very good.

Lasting qualities of cut flowers: Very good.

Vegetation: Very vigorous.

Resistance of the plant to diseases: As observed for several years in the cultures at Cagnes-sur-Mer (A.M.) France. Very good for the chief diseases which affect roses in industrial culture.

We claim:

1. A new and distinct rose variety of the class of the tea hybrid, characterized by its large and beautiful flowers between Currant Red and Blood Red in color with tonalities of Red Rose in the center of the flower, its suitability for cut flower production and for ornamental plants, with a dense and bushy vegetation, large and dark foliage, highly productive in cut flower culture, its resistance to disease, ease of propagation and suitability for ornamental purposes, substantially as described and specified.

No references cited.

ROBERT E. BAGWILL, *Primary Examiner.*